United States Patent [19]
Rettig et al.

[11] Patent Number: 5,587,299
[45] Date of Patent: Dec. 24, 1996

[54] ISOLATED NUCLEIC ACID MOLECULE CODING FOR FIBROBLAST ACTIVATION PROTEIN ALPHA AND USES THEREOF

[75] Inventors: Wolfgang J. Rettig, Biberach, Germany; Matthew J. Scanlan, New York, N.Y.; Pilar Garin-Chesa, Biberach, Germany; Lloyd J. Old, New York, N.Y.

[73] Assignee: Memorial Sloan-Kettering Cancer Center, New York, N.Y.

[21] Appl. No.: 230,491

[22] Filed: Apr. 20, 1994

[51] Int. Cl.$^6$ .......................... C12N 15/12; C12N 15/19
[52] U.S. Cl. .................. 435/69.1; 435/6; 435/240.2; 435/252.3; 435/320.1; 435/252.33; 536/23.5
[58] Field of Search .................. 435/6, 7.1, 7.2, 435/240.2, 252.3, 252.33, 320.1, 69.1; 536/23.5

[56] References Cited

PUBLICATIONS

Rettig, W., et al., Cancer Research, 53:3327–3335, 1993.
Rettig, W. et al., PNAS, 85:3110–3114, 1988.
Aruffo, A. et al., PNAS, 84:8573–8577, 1987.

Primary Examiner—Marianne P. Allen
Attorney, Agent, or Firm—Felfe & Lynch

[57] ABSTRACT

The invention describes the identification and isolation of nucleic acid molecules which code for fibroblast activation protein alpha, or "FAPα". Various applications of the isolated molecules are also described.

15 Claims, 5 Drawing Sheets

```
FAP    1  MKTWVKIVFGV*ATSAVLALLVMCIVLRPSRVHNSEENTMRALTLKDILN   49
CD26   1  ---PW-VLL-LLGAA-LVTIITVPV--LNKGTDDATADSRKTY--T-Y-K   50

FAP   50  GTFSYKTFFPNWISGQEYLHQSADNNIVLYNIETGQSYTILSNRTMKSV*   98
CD26  51  N-YRL-LYSLR---DH---YKQ*E---LVF-A-Y-N-SVF-E-S-FDEFG   99

FAP   99  *NASNYGLSPDRQFVYLESDYSKLWRYSYTATYYIYDLSNGEFVRGNELP  147
CD26 100  HSIND-SI---G--IL--YN-V-Q--H----S-D----NKRQLITEERI-  149
                                                    fap-1
FAP  148  RPIQYLCWSPVGSKLAYVYQNNIYLKQRPGDPPFQITFNGRENKIFNGIP  197
CD26 150  NNT-WVT-----H-----WN-D--V-IE-NL-SYR--WT-K-DI-Y---T  199
                              fap-2
FAP  198  DWVYEEEMLPTKYALWWSPNGKFLAYAEFNDKDIPVIAYSYYGDE**QYP  245
CD26 200  -------VFSAYS---------T-----Q---TEV-L-E--F-S--SL---  249

FAP  246  RTINIPYPKAGAKNPVVRIFIIDT***TYPAYVGPQEVPVPAMIASSDYY  292
CD26 250  K-VRV-------V--T-KF-VVN-DSLSSVTNATSIQITA--SMLIG-H-  299

FAP  293  FSWLTWVTDERVCLQWLKRVQNVSVLSICDFREDWQTWDCPKTQEHIEES  342
CD26 300  LCDV--A-Q--IS----R-I--Y--MD---YD-SSGR-N-LVARQ---M-  349

FAP  343  RTGWAGGFFVSRPVFSYDAISYYKIFSDKDGYKHIHYIKDTVENAIQITS  392
CD26 350  T---V-R-RP-E-H-TL-GN-F---I-NEE--R--C-FQIDKKDCTF--K  399

FAP  393  GKWEAINIFRVTQDSLFYSSNEFEEYPGRRNIYRISIGSYPPSKKCVTCH  442
CD26 400  -T--V-G-EAL-S-Y-Y-I---YKGM--G--L-K-QLSD-T*KVT-LS-E  448

FAP  443  LRKERCQYYTASFSDYAKYYALVCYGPGIPISTLHDGRTDQEIKILEENK  492
CD26 449  -NP------SV---KE----Q-R-S---L-LY---SSVN-KGLRV--D-S  498
                               fap-3
FAP  493  ELENALKNIQLPKEEIKKLEVDEITLWYKMILPPQFDRSKKYPLLIQVYG  542
CD26 499  A-DKM-Q-V-M-SKKLDFIILN-TKF--Q-----H--K-------LD--A  548

FAP  543  GPCSQSVRSVFAVNWISYLASKEGMVIALVDGRGTAFQGDKLLYAVYRKL  592
CD26 549  -----KADT--RL--AT----T-NIIV-SF----SGY----IMH-IN-R-  598

FAP  593  GVYEVEDQITAVRKFIEMGFIDEKRIAIWGWSYEIRFITGPCIWNWSFQM  642
CD26 599  -TF------E-A-Q-SK---V-N---------GGYVTSMVLGSGSVGFK  648

FAP  643  WYSSGSSLQLGILRVCLHRE*IHGSPNKDDNLEHYKNSTVMARAEYFRNV  691
CD26 649  CGIAVAPVSRWEYYDSVYT-RYM-L-TPE---D--R-----S---N-KQ-  698

FAP  692  DYLLIHGTADDNVHFQNSAQIAKALVNAQVDFQAMWYSDQNHGLSGLSTN  741
CD26 699  E--------------Q----S----DVG--------T-ED--IASSTAH  748

FAP  742  *HLYTHMTHFLKQCFSLSD
CD26 749  Q-I----S--I------P
```

| | Breast Cancer | MFH | Healing Wound | Renal Cancer |
|---|---|---|---|---|
| FAPα | (+)<br>A | (+)<br>C | (+)<br>E | (−)<br>G |
| CD26 | (−)<br>B | (−)<br>D | (+)<br>F | (+)<br>H |

Immunohistochemistry (See Kodachromes)

ISOLATED NUCLEIC ACID MOLECULE CODING FOR FIBROBLAST ACTIVATION PROTEIN ALPHA AND USES THEREOF

FIELD OF THE INVENTION

This invention relates to certain molecules associated with cancer cells and reactive with tumor stromal cells. More particularly, it relates to fibroblast activation protein alpha ("FAPα" hereafter). The molecule has previously been identified immunologically, but nucleic acid molecules coding for it had not been isolated or cloned. This, inter alia, is the subject of the invention. The protein has a molecular weight of from about 88 to about 95 kilodaltons as determined by SDS-PAGE. This molecule is characterized by a number of features and properties which are shared by and characteristic of membrane bound enzymes, suggesting very strongly that it, too, is a membrane bound enzyme. The nucleic acid molecules, which are a key part of the invention, are useful both as probes for cells expressing FAPα, and as starting materials for recombinant production of the protein. The recombinant protein can then be used to produce monoclonal antibodies specific for the protein, and are these useful diagnostic agents themselves.

BACKGROUND AND PRIOR ART

The invasive growth of epithelial cancers is associated with characteristic cellular and molecular changes in the supporting stroma. For example, epithelial cancers induce the formation of tumor blood vessels, the recruitment of reactive tumor stromal fibroblasts, lymphoid and phagocytic infiltrates, the release of peptide mediators and proteolytic enzymes, and the production of an altered extracellular matrix (ECM). See, e.g., Folkman, Adv. Cancer Res. 43: 175–203 (1985); Basset et al., Nature 348: 699–704 (1990); Denekamp et al., Cancer Metastasis Rev. 9: 267–282 (1990); Cullen et al., Cancer Res. 51:4978–4985 (1991); Dvorak et al., Cancer Cells 3:77–85 (1991); Liotta et al., Cancer Res. 51: 5054s–5059s (1991); Garin-Chesa et al., J. Histochem. Cytochem. 37:1767–1776 (1989). A highly consistent molecular trait of the stroma in several common histologic types of epithelial cancers is induction of the fibroblast activation protein (FAPα), a cell surface glycoprotein with an observed $M_r$ of 95,000 originally discovered with a monoclonal antibody, mAb F19, raised against proliferating cultured fibroblasts. See Rettig et al., Cancer Res. 46:6406–6412 (1986); Rettig et al., Proc. Natl. Acad. Sci. USA 85: 3110–3114 (1988); Garin-Chesa et al., Proc. Natl. Acad. USA 87: 7235–7239 (1990); Rettig et al., Cancer Res. 53:3327–3335 (1993). Each of these four papers is incorporated by reference in its entirety.

Immunohistochemical studies such as those cited supra have shown that FAPα is transiently expressed in certain normal fetal mesenchymal tissues but that normal adult tissues are generally FAPα⁻. Similarly, malignant epithelial, neural and hematopoietic cells are FAPα⁻. However, most of the common types of epithelial cancers, including >90% of breast, lung, skin, pancreas, and colorectal carcinomas, contain abundant FAPα⁺ reactive stromal fibroblasts. Garin-Chesa et al., Proc. Natl. Acad. Sci. USA 87: 7235–7239 (1990). The FAPα⁺ tumor stromal fibroblasts almost invariably accompany newly-formed tumor blood vessels, forming a distinct cellular compartment interposed between the tumor capillary endothelium and the basal aspect of malignant epithelial cell clusters. While FAPα⁺ stromal fibroblasts are found in both primary and metastatic carcinomas, benign and premalignant epithelial lesions, such as fibroadenomas of the breast and colorectal adenomas only rarely contain FAPα⁺ stromal cells. In contrast to the stroma-specific localization of FAPα⁺ in epithelial neoplasms, FAPα is expressed in the malignant cells of a large proportion of bone and soft tissue sarcomas. Rettig et al., Proc. Natl. Acad. Sci. USA 85: 3110–3114 (1988). Finally, FAPα⁺ fibroblasts have been detected in the granulation tissue of healing wounds (Garin-Chesa et al., Supra). Based on the restricted distribution pattern of FAPα in normal tissues and its uniform expression in the supporting stroma of many epithelial cancers, clinical trials with ¹³¹I-labeled mAb F19 have been initiated in patients with metastatic colon cancer (Welt et al., Proc. Am. Assoc. Cancer Res. 33:319 (1992)) to explore the concept of "tumor stromal targeting" for immunodetection and immunotherapy of epithelial cancers.

The induction of FAPα⁺ fibroblasts at times and sites of tissue remodeling during fetal development, tissue repair, and carcinogenesis is consistent with a fundamental role for this molecule in normal fibroblast physiology. Thus, it is of interest and value to isolate and to clone nucleic acid molecules which code for this molecule. This is one aspect of the invention, which is described in detail together with other features of the invention, in the disclosure which follows.

BRIEF DESCRIPTION OF THE FIGURES

FIG. 1 shows results obtained from immunoprecipitation studies carried out on detergent extracts of Trans ³⁵S-labeled cells. The study was designed to immunoprecipitate FAPα and CD26. Cell types were SW872, which is a human sarcoma cell line, COS-FAP, which is a cell line transfected with a vector coding for FAPα, i.e., pFAP-38, described in the application, and COS-CD26, which is a COS cell line transfected with a CD26 coding plasmid. Extracts were precipitated with anti-FAPα monoclonal antibody F19, anti-CD26 mAb EF-1, or a negative control mouse Ig.

FIG. 3 compares the deduced amino acid sequence for FAPα, and the known sequence of CD26. The alignment has been optimized.

In FIGS. 5A and 5B, breast cancer is studied, for FAPα (FIG. 5A), and CD26 (FIG. 5B). In FIGS. 5C and 5D, malignant fibrous histiocytomas are studied, for FAPα (FIG. 5C), and CD26 (FIG. 5D). Dermal scar tissue is examined in FIGS. 5E (FAPα), and 5F (CD26). Renal cell carcinoma is studied in FIG. 5G (FAPα), and 5H (CD26).

DETAILED DESCRIPTION OF PREFERRED EMBODIMENTS

EXAMPLE 1

Fibroblast cell line WI-38 had been observed, previously, to react with mAb F19 (Rettig et al., Canc. Res. 46:6406–6412 (1986); Rettig et al., Proc. Natl. Acad. USA 85: 3110–3114 (1988); Garin-Chesa et al., Proc. Natl. Acad. Sci. USA 87: 7235–7239 (1990); Rettig et al., Canc. Res. 53: 3327–3335 (1993)). It was used in the experiments which follow.

A cDNA library was prepared from WI-38, using well known techniques and commercially available materials. Specifically, the library was constructed in expression vector pCDNAI, using the Fast Track mRNA isolation kit, and Librarium cDNA phagemid system. Once the library was prepared, the vectors were electroporated into cell line E. coli MC 1061/P3. The pCDNAI expression vector contains an antibiotic resistance gene, so the E. coli were selected via antibiotic resistance. The colonies which were resistant were then used in further experiments. The plasmid DNA from the colonies was obtained via alkaline lysis and purification on CsCl$_2$, in accordance with Sambrook et al, Molecular Cloning: A Laboratory Manual (Cold Spring Harbor Lab, Cold Spring Harbor, N.Y. 2d Ed. 1989). The technique is well known to the art, but is incorporated by reference herein.

Once the plasmid DNA was isolated, it was used to transfect COS-1 cells, which were then cultured for forty-eight hours, after which these were tested with antibody coated dishes. The mAbs used included F19, as described by Rettig et al., (1986), supra, which is incorporated by reference in its entirety. As COS-1 cells are normally FAPα$^-$, any positive results indicated the presence of the coding sequence. The immunoselection protocol was that of Aruffo et al., Proc. Natl. Acad. Sci USA 84: 3365–3369 (1987), incorporated by reference herein.

Plasmid DNA from positive clones was recovered, in accordance with Hirt, J. Mol. Biol. 26: 365–369 (1967), reintroduced into E. coli MC 1061/P3, and reselected into COS-1 cells.

The protocol presented herein was followed for four rounds. After this, the plasmid DNA of 50 isolated bacterial colonies was purified, using the Qiagen plasmid kit. Of the colonies, 27 clones were found to contain identical 2.8 kb inserts, as determined by EcoRI restriction enzyme mapping. Several of these were found to contain FAPα-specific cDNA, via transient expression in COS-1 cells and direct immunofluorescence staining. One of these clones, i.e., "pFAP.38" was selected for further study, as elaborated upon infra.

EXAMPLE 2

Once pFAP.38 had been identified, it was tested together with a vector coding for known cell surface marker CD26 ("pCD26"), as well as with control vector pCDNA I.

In these experiments, COS-1 cells were transfected with one of pFAP.38, pCD26, or pCDNAI. After forty-eight hours, the transfectants were tested, using the well known MHA rosetting assay for cell surface antigen expression. In these experiments, mAb F19, which is FAPα specific, was used, together with mAb EF-1, which is CD26 specific. Also used were four other FAPα specific mAbs, i.e., FB23, FB52, FB58 and C48. Also tested were two cancer cell lines, which are known to react with mAb F19 (SW872 liposarcoma), or EF-1 (SK-OV6 ovarian cancer). The results are set forth in Table 1, which follows.

TABLE 1

Cell surface expression of multiple FAPα epitopes and CD26 in human cells and COS-1 cell transfectants.

| Target cell | Cell surface antigen expresion | | | | | |
| --- | --- | --- | --- | --- | --- | --- |
| | F19 | FB23 | FB52 | FB58 | C48 | EF-1 |
| Human cells | | | | | | |
| SW872 liposarcoma | >95% | >95% | >95% | >95% | >95% | — |
| SK-OV6 ovarian cancer | — | — | — | — | — | >95% |
| COS.1 transfectants | | | | | | |
| COS.pCDNAI control | — | — | — | — | — | — |
| COS.pFAP38 | 40% | 30% | 40% | 20% | 20% | — |
| COS.pCD26 | — | — | — | — | — | 40% |

EXAMPLE 3

Immunoprecipitation studies were then carried out to identify the antigen being targeted by the antibodies.

Cells were metabolically labelled with Trans $^{35}$S-label, (ICN), extracted with lysis buffer (0.01M Tris-HCl/0.15M NaCl/0.01M MgCl$_2$/0.5% Nonidet P-40/aprotinin (20 ug/ml)/2 mM phenylmethylsulfonyl fluoride), and then immunoprecipitated. The protocols used are all well known, as will be seen by reference to Rettig et al., Canc. Res. 53:3327–3335 (1993); and Fellinger et al., Canc. Res. 51: 336–340 (1991), the disclosures of which are all incorporated by reference in their entirety. Precipitating mAbs were negative control mouse Ig, mAb F19, or EF-1. Control tests were carried out with mock transfected COS-1 cells. Following immunoprecipitation, the immunoprecipitates were separated on NaDOdSO$_4$/PAGE, under reducing conditions. In some experiments, an additional test was carried out to determine whether or not the immunoprecipitated material was glycosylated. In these experiments, cell extracts were fractionated with Con A-SEPHAROSE prior to immunoprecipitation. Following immunoprecipitation, but prior to fractionation on NaDodSO$_4$/PAGE, these precipitates were digested with N-Glycanase.

Figure 1:
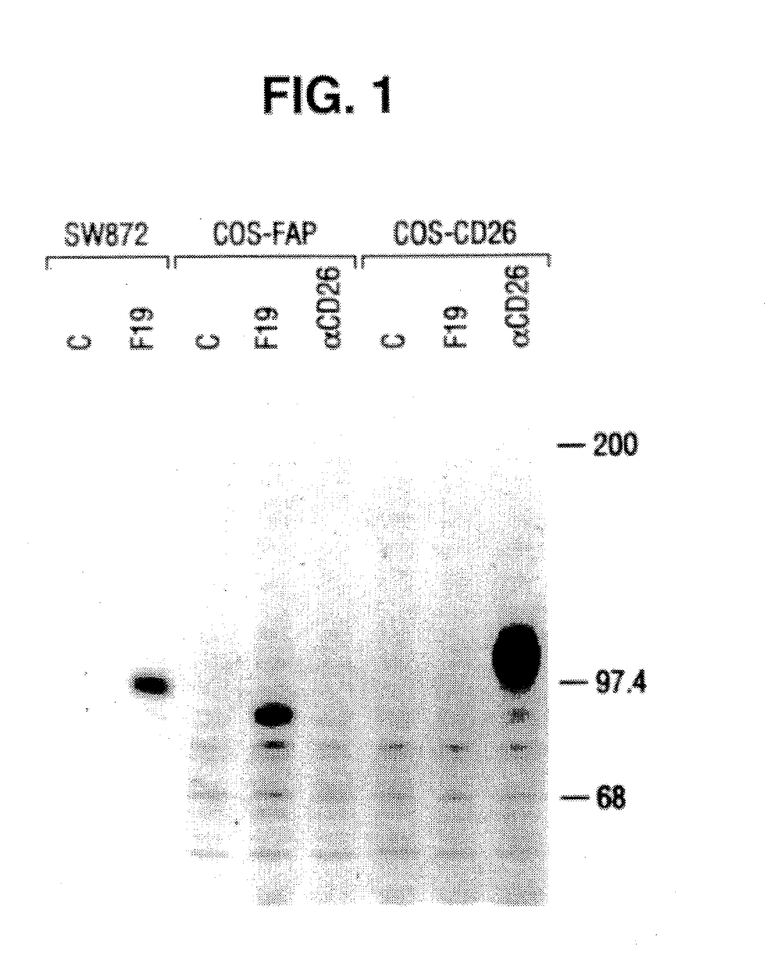

The results are shown in FIG. 1. In COS-1 cells, pFAP.38 directs expression of an 88 kd protein species (as determined via SDS-PAGE), which is slightly smaller than the 95 kd FAPα species produced by SW872, or cultured fibroblasts. Digestion with N-Glycanase produced peptides of comparable size (i.e., 74 kd versus 75 kd), showing that the glycosylation of the FAPα protein in COS-1 cells is different than in the human cell lines.

EXAMPLE 4

Classic Northern blot analysis was then carried out, using the mRNA from FAPα$^+$ fibroblast cell lines WI-38 and GM 05389, and FAPα⁻ ovarian cancer cell line SK-OV6. Using the procedures of Sambrook et al., supra, five micrograms of mRNA from each cell line were tested. The probes used were $^{32}$p labelled, and were prepared from a 2.3 kb EcoRI fragment of pFAP.38, a 2.4 kb Hind III fragment of CD26, and a 1.8 kb BamHI fragment of γ-actin cDNA. These fragments had been purified from 1% agarose gels.

Figure 2A:
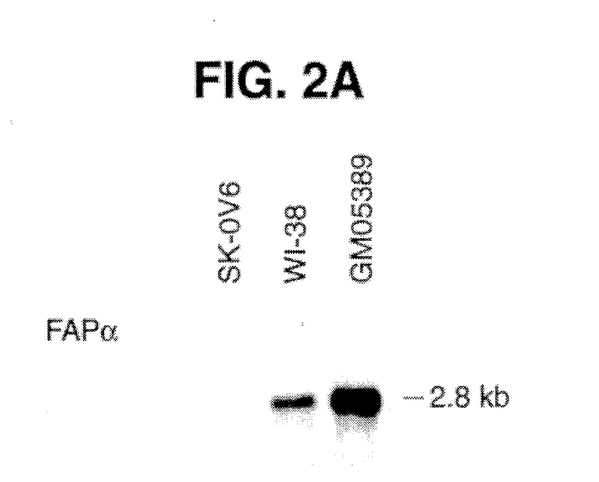
FIG. 2A presents Northern blot analysis of FAPα expression in a cell line (ovarian cancer SK-OV6), which has FAPα⁻/CD26⁺ phenotype), as well as two cell lines (fibroblasts WI-38 and GM 05389), which have FAPα⁺/CD26⁺ phenotype.
Figure 2B:
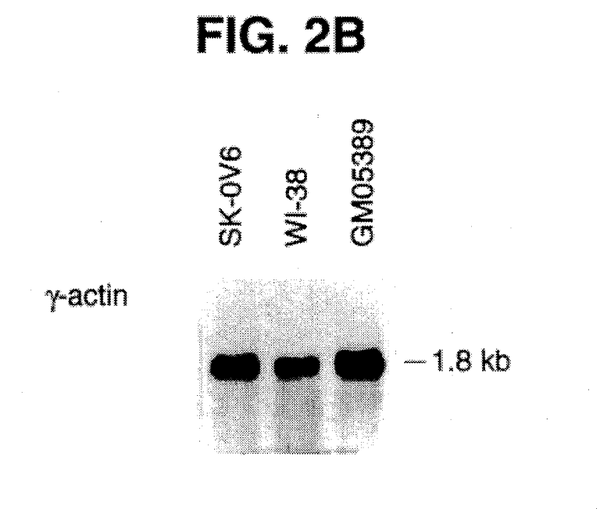
FIG. 2B shows γ-actin expression for the cell lines of FIG. 2A.

FIG. 2 presents these results. The extracts of FAPα⁺ fibroblast strains show a 2.8 kb FAP mRNA species, but extracts of SK-OV6 do not. A γ-actin mRNA species (1.8 kb), is seen in all species.

EXAMPLE 5

The cDNA identified as coding for FAPα was subjected to more detailed analysis, starting with sequencing. The classic Sanger methodology, as set forth in Proc. Natl. Acad. Sci. USA 74: 5463–5467 (1977), was used to sequence both strands of the cDNA. Once this was secured, an amino acid sequence was deduced therefrom. This information is presented in SEQ ID NO: 1. The sequence was then compared to the known amino acid sequence of CD26 (Morimoto et al., J. Immunol. 143:3430–3437 (1989)). FIG. 3 presents the comparison, using optimized sequence alignment. Any gaps in the comparison are indicated by asterisks, while identical amino acids are shown by dashes in the CD26 sequence. A hydrophobic, putative transmembrane sequence is double underlined, while potential N-glycosylation sites are single underlined.

The sequence analysis shows a 2815 base pair insert, wherein 2280 base pairs constitute the open reading frame. This ORF extends from start codon ATG at nucleotide 209, to stop codon TAA at 2486.

The deduced peptide is 760 amino acids long, and has a molecular weight of 87,800. In contrast, N-Glycanase digested, immunopurified FAPα was reported to have an estimated $M_r$ of 75,000 on NaDodSO$_4$/PAGE (Rettig et al., Canc. Res. 53:3327–3335 (1993)). A TATA box is found 83 base pairs upstream of the start codon. A polyadenylation signal and a poly-A tail were found in the 5'-untranslated region of the insert.

A GenBank data base search was then carried out. The most closely related genes found were those encoding dipeptidyl peptidase IV homologues (DPPIV; EC 3.4.14.5), with human DPPIV (also known as T-cell activation antigen CD26), showing 51% nucleotide sequence identity, and 52% amino acid sequence identity.

The second set of related genes are human, rat, and bovine homologues of DPPX, a gene of unknown function widely expressed in brain and other normal tissues. The predicted human DPPX gene product shows about 30% amino acid sequence identity with FAPα and CD26. The FAPα molecule exhibits structural features typical of type II integral membrane proteins, including a large COOH-terminal extracellular domain, a hydrophobic transmembrane segment, and a short cytoplasmic tail. The putative extracellular domain contains five potential N-glycosylation sites, 12 cysteine residues (9 of which are conserved between FAPα and CD26), and three segments corresponding to highly conserved catalytic domains characteristic of serine proteases, such as DPPIV. These conserved sequences are presented in Table 2, which follows. Comparisons to DPPIV and DPPX were made via Morimoto et al., supra; Wada et al., Proc. Natl. Acad. Sci. USA 89: 197–201 (1992); Yokotani et al., Human Mol. Genet. 2: 1037–1039 (1993).

TABLE 2

Putative catalytic domains of FAPα, DPPIV and DPPX.

| | 625 | 701 | 733 |
| --- | --- | --- | --- |
| Human FAPα | WGWSYEI | GTADDNV | DQNHGLS |
| Human DPPIV | WGWSYGG | GTADDNV | DEDHGIA |
| Mouse DPPIV | WGWSYGG | GTADDNV | DEDHGIA |
| Rat DPPIV | WGWSYGG | GTADDNV | DEDHGIA |
| Yeast DPPIV | FGWSYGG | GTGDDNV | DSDHSIR |
| Human DPPX | FGKDYGG | PTADEKI | DESHYFT |
| Rat DPPX | FGKDYGG | ATADEKI | DESHYFII |
| Bovine DPPX | FGKDYGG | ATADEKI | DESHYFS |

EXAMPLE 6

An additional set of experiments were carried out to determine whether FAPα related sequences are present in non-human species. To do so, human, mouse, and Chinese hamster genomic DNA was digested using restriction enzymes, and tested, via Southern blotting, using the 2.3 kb fragment labelled with $^{32}$p describes supra. Hybridization was carried out using stringent washing conditions (0.1× SSC, 0.1% NaDodSO$_4$, 68° C.). Cross-hybridization was readily observed with both the mouse and hamster DNA, suggesting the existence of highly conserved FAPα homologues. In control experiments using the CD26 cDNA fragment described supra, no evidence of cross hybridization was observed.

EXAMPLE 7

The CD26 molecule shares a number of biochemical and serological properties with FAPβ, which is a previously described, FAPα associated molecule having a molecular weight of 105 kd, and found on cultured fibroblasts and melanocytes (Rettig et al., Canc. Res. 53: 3327–3335 (1993)). Cotransfection experiments were carried out to determine whether FAPβ is a CD26 gene product. To test this, the same protocols were used which were used for transfection with pFAP.38 or pCD26, as described Supra, but using the two vectors. The results presented supra showed that cotransfection efficiency was about 40% for each vector, so about 10–20% of cell should be cotransfected.

Following cotransfection, the COS-1 cells were Trans $^{35}$S-labeled, as described supra, then lysed, also as described supra.

The resulting cell extracts were separated on Con A SEPHAROSE, and the antigen (FAPα and/or CD26) were recovered in the Con A-bound fraction. The bound fraction was eluted with 0.25M α-D-mannopyranoside. Immunoprecipitation was then carried out, as described supra, and the precipitates were separated on NaDodSO$_4$/PAGE, also as discussed supra.

Figure 4:
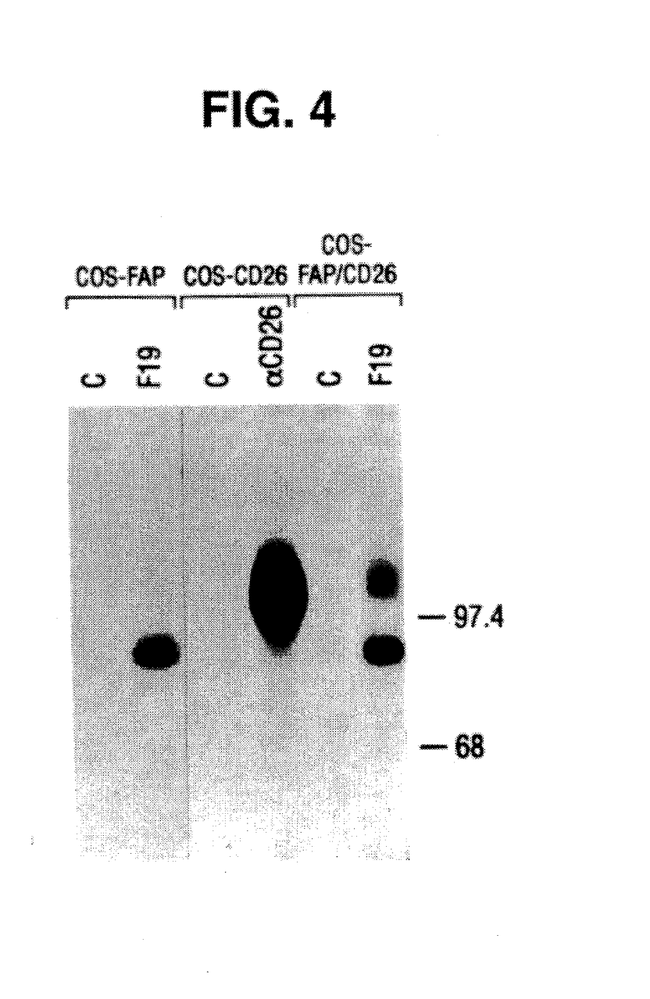
FIG. 4 depicts heterodimer formation between FAPα and CD26 in COS-1 transfectants.

FIG. 4 shows these results, together with results from single transfection experiments. Those cells transfected only with pFAP.38 produce FAPα, but not FAPβ (determined from mAb F19 immunoprecipitates). They also produce no CD26 antigen (tested with EF-1). Those cells transfected with pCD26 alone produce CD26 but no FAPα. Cotransfectants produce CD26 and FABα/FAPβ heteromers, as determined in the mAb F19 precipitates. This result provides direct evidence that FAPβ is a CD26 gene product.

EXAMPLE 8

It has been observed previously that some cultured human cell types coexpress FAPα and CD26, and show FAPα/CD26 heteromer formation. In vivo distribution patterns of FAPα and CD26, however, as determined in previous immunohistochemical studies, appeared to be non-overlapping. (See Rettig et al., Proc. Natl. Acad. Sci. USA 85: 3110–3114 (1988); Garin-Chesa et al., Proc. Natl. Acad. Sci. USA 87: 7235–7329 (1990); Rettig et al., Canc. Res. 53: 3327–3335 (1993); Stein et al., in Knapp et al., eds. Leukocyte typing IV-white cell differentiation antigens, pp 412–415 (Oxford University Press, N.Y. 1989), pp. 412–415; Möbious et al., J. Exp. Immunol. 74: 431–437 (1988)). In view of the potential significance of FAPα/CD26 coassociation, tissue distribution was reexamined, via side by side immunohistochemical staining of normal tissues and lesional tissues known to contain FAPα$^+$ fibroblasts or FAPα$^+$ malignant cells.

To test the samples, they were embedded in OCT compound, frozen in isopentane precooled in liquid nitrogen, and stored at −70° C. until used. Five micrometer thick sections were cut, mounted on poly-L-lysine coated slides, air dried, and fixed in cold acetone (4° C., for 10 minutes). The sections were then tested with mAbs (10–20 ug/ml), using the well known avidin-biotin immmunoperoxidase method, as described by, e.g., Garin-Chesa et al., J. Histochem. Cytochem. 37: 1767–1776 (1989); Garin-Chesa et al., Proc. Natl. Acad. Sci. USA 87: 7235–7239 (1990); Rettig et al., Canc. Res. 53:3327–3335 (1993); Garin-Chesa et al., Am. J. Pathol. 142: 557–567.

Figure 5:
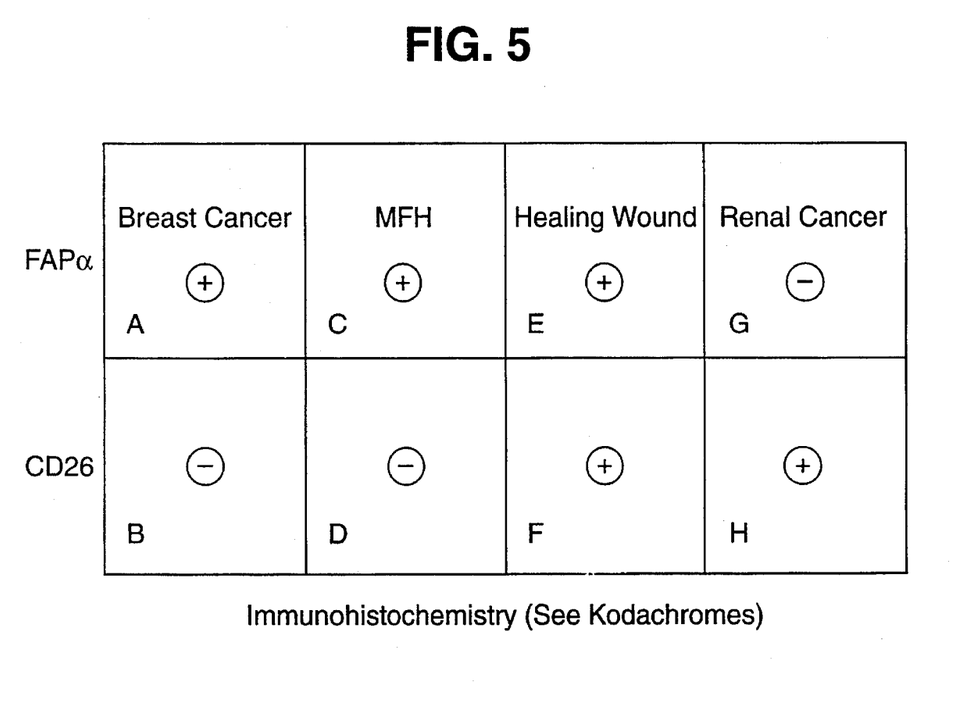
FIGS. 5A–5H, inclusive, display immunohistochemical detection of FAPα and CD26 in various cancers.

The results are shown in FIG. 5. Breast, colorectal, pancreas and lung carcinomas showed strong expression of FAPα and not CD26 was found (see FIGS. 5A and 5B). Five FAPα$^+$ sarcomas, including malignant fibrous histocytoma (FIGS. 5C and 5D), were tested, and there was no expression of CD26. Examination of reactive fibroblasts of healing dermal wounds (FIGS. 5E, 5F), showed abundant expression of both FAPα and CD26. The three renal carcinomas tested (FIGS. 5G, 5H), showed expression of CD26 in malignant epithelium. FAPα was absent from malignant epithelial cells, and showed low expression in the stroma of these carcinomas.

The foregoing examples describe an isolated nucleic acid molecule which codes for fibroblast activating protein alpha ("FAPα"). The expression product of the sequence is a protein which, on SDS-PAGE, shows a molecular weight of about 75 kd. Deduced amino acid sequence, as provided in SEQ ID NO: 1, for one form of the molecule, yields a molecular weight of about 88 kd. It is to be understood that, as described, FAPα may be glycosylated, with the type and amount of glycosylation varying, depending upon the type of cell expressing the molecule. The experiment described herein shows this.

The invention also comprehends the production of expression vectors useful in producing the FAPα molecule. In their broadest aspect, these vectors comprise a FAPα coding sequence, operably linked to a promoter. Additional elements may be a part of the expression vector, such as genes which confer antibiotic resistance, amplifiable genes, and so forth.

The coding sequences and vectors may also be used to prepare cell lines, wherein the coding sequence or expression vector is used to transfect or to transform a recipient host. The type of cell used maybe prokaryotic, such as E. coli, or eukaryotes, such as yeast, CHO, COS, or other cell types.

The identification of nucleic acid molecules such as that set forth in SEQ ID NO: 1 also enables the artisan to identify and to isolate those nucleic acid molecules which hybridize to it under stringent conditions. "Stringent condition" as used herein, refers to those parameters set forth supra, whereby both murine and hamster sequences were also identified. It will be recognized by the skilled artisan that these conditions afford a degree of stringency which can be achieved using parameters which vary from those recited. Such variance is apprehended by the expression "stringent conditions".

The ability of nucleic acid molecules to hybridize to complementary molecules also enables the artisan to identify cells which express FAPα, via the use of a nucleic acid hybridization assay. One may use the sequences described in the invention to hybridize to complementary sequences, and thus identify them. In this way, one can target mRNA, e.g., which is present in any cell expressing the FAPα molecule.

It is of course understood that the nucleic acid molecules of the invention are also useful in the production of recombinant FAPα. The recombinant protein may be used, e.g., as a source of an immunogen for generation of antibodies akin to known mAb F19, and with the same uses. Similarly, the recombinant protein, and/or cells which express the molecule on its surface, may be used in assays to determine antagonists, agonists, or other molecules which interact with the FAPα molecule. Such molecules may be, but are not necessarily limited to, substrates, inhibiting molecules, antibodies, and so forth. This last feature of the invention should be considered in light of the observed structural resemblances to membrane bound enzymes. This type of molecule is associated with certain properties which need not be described in detail here. It will suffice to say that inhibition or potentiation of these properties as associated with FAPα is a feature of this invention. For example, one may identify substrates or the substrate for the FAPα molecule, via the use of recombinant cells or recombinant FAPα per se. The substrates can be modified to improve their effect, to lessen their effect, or simply to label them with detectable signals so that they can be used, e.g., to identify cells which express FAPα. Study of the interaction of substrate and FAPα, as well as that between FAPα and any molecule whatsoever, can be used to develop and/or to identify agonists and antagonists of the FAPα molecule.

Other aspects of the invention will be clear to the skilled artisan, and need not be set forth here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

5,587,299

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 2815 Base pairs
        ( B ) TYPE: nucleic acid
        ( C ) STRANDEDNESS: double
        ( D ) TOPOLOGY: linear     ( x i ) SEQUENCE DESCRIPTION: SEQ ID NO: 1:

```
AAGAACGCCC  CCAAAATCTG  TTTCTAATTT  TACAGAAATC  TTTTGAAACT  TGGCACGGTA     60
TTCAAAAGTC  CGTGGAAAGA  AAAAAACCTT  GTCCTGGCTT  CAGCTTCCAA  CTACAAAGAC    120
AGACTTGGTC  CTTTTCAACG  GTTTTCACAG  ATCCAGTGAC  CCACGCTCTG  AAGACAGAAT    180
TAGCTAACTT  TCAAAAACAT  CTGGAAAAAT  GAAGACTTGG  GTAAAAATCG  TATTTGGAGT    240
TGCCACCTCT  GCTGTGCTTG  CCTTATTGGT  GATGTGCATT  GTCTTACGCC  CTTCAAGAGT    300
TCATAACTCT  GAAGAAAATA  CAATGAGAGC  ACTCACACTG  AAGGATATTT  TAAATGGAAC    360
ATTTTCTTAT  AAAACATTTT  TTCCAAACTG  GATTTCAGGA  CAAGAATATC  TTCATCAATC    420
TGCAGATAAC  AATATAGTAC  TTTATAATAT  TGAAACAGGA  CAATCATATA  CCATTTTGAG    480
TAATAGAACC  ATGAAAAGTG  TGAATGCTTC  AAATTACGGC  TTATCACCTG  ATCGGCAATT    540
TGTATATCTA  GAAAGTGATT  ATTCAAAGCT  TTGGAGATAC  TCTTACACAG  CAACATATTA    600
CATCTATGAC  CTTAGCAATG  GAGAATTTGT  AAGAGGAAAT  GAGCTTCCTC  GTCCAATTCA    660
GTATTTATGC  TGGTCGCCTG  TTGGGAGTAA  ATTAGCATAT  GTCTATCAAA  ACAATATCTA    720
TTTGAAACAA  AGACCAGGAG  ATCCACCTTT  TCAAATAACA  TTTAATGGAA  GAGAAAATAA    780
AATATTTAAT  GGAATCCCAG  ACTGGGTTTA  TGAAGAGGAA  ATGCTTCCTA  CAAAATATGC    840
TCTCTGGTGG  TCTCCTAATG  GAAAATTTTT  GGCATATGCG  GAATTTAATG  ATAAGGATAT    900
ACCAGTTATT  GCCTATTCCT  ATTATGGCGA  TGAACAATAT  CCTAGAACAA  TAAATATTCC    960
ATACCCAAAG  GCTGGAGCTA  AGAATCCCGT  TGTTCGGATA  TTTATTATCG  ATACCACTTA   1020
CCCTGCGTAT  GTAGGTCCCC  AGGAAGTGCC  TGTTCCAGCA  ATGATAGCCT  CAAGTGATTA   1080
TTATTTCAGT  TGGCTCACGT  GGGTTACTGA  TGAACGAGTA  TGTTTGCAGT  GGCTAAAAAG   1140
AGTCCAGAAT  GTTTCGGTCC  TGTCTATATG  TGACTTCAGG  GAAGACTGGC  AGACATGGGA   1200
TTGTCCAAAG  ACCCAGGAGC  ATATAGAAGA  AAGCAGAACT  GGATGGGCTG  GTGGATTCTT   1260
TGTTTCAAGA  CCAGTTTTCA  GCTATGATGC  CATTTCGTAC  TACAAAATAT  TTAGTGACAA   1320
GGATGGCTAC  AAACATATTC  ACTATATCAA  AGACACTGTG  GAAAATGCTA  TTCAAATTAC   1380
AAGTGGCAAG  TGGGAGGCCA  TAAATATATT  CAGAGTAACA  CAGGATTCAC  TGTTTTATTC   1440
TAGCAATGAA  TTTGAAGAAT  ACCCTGGAAG  AAGAAACATC  TACAGAATTA  GCATTGGAAG   1500
CTATCCTCCA  AGCAAGAAGT  GTGTTACTTG  CCATCTAAGG  AAAGAAGGT  GCCAATATTA   1560
CACAGCAAGT  TTCAGCGACT  ACGCCAAGTA  CTATGCACTT  GTCTGCTACG  GCCCAGGCAT   1620
CCCCATTTCC  ACCCTTCATG  ATGGACGCAC  TGATCAAGAA  ATTAAAATCC  TGGAAGAAAA   1680
CAAGGAATTG  GAAAATGCTT  TGAAAAATAT  CCAGCTGCCT  AAAGAGGAAA  TTAAGAAACT   1740
TGAAGTAGAT  GAAATTACTT  TATGGTACAA  GATGATTCTT  CCTCCTCAAT  TTGACAGATC   1800
AAAGAAGTAT  CCCTTGCTAA  TTCAAGTGTA  TGGTGGTCCC  TGCAGTCAGA  GTGTAAGGTC   1860
```

-continued

```
TGTATTTGCT  GTTAATTGGA  TATCTTATCT  TGCAAGTAAG  GAAGGGATGG  TCATTGCCTT  1920
GGTGGATGGT  CGAGGAACAG  CTTTCCAAGG  TGACAAACTC  CTCTATGCAG  TGTATCGAAA  1980
GCTGGGTGTT  TATGAAGTTG  AAGACCAGAT  TACAGCTGTC  AGAAAATTCA  TAGAAATGGG  2040
TTTCATTGAT  GAAAAAAGAA  TAGCCATATG  GGGCTGGTCC  TATGGAGGAT  ACGTTTCATC  2100
ACTGGCCCTT  GCATCTGGAA  CTGGTCTTTT  CAAATGTGGT  ATAGCAGTGG  CTCCAGTCTC  2160
CAGCTGGGAA  TATTACGCGT  CTGTCTACAC  AGAGAGATTC  ATGGGTCTCC  CAACAAGGA   2220
TGATAATCTT  GAGCACTATA  AGAATTCAAC  TGTGATGGCA  AGAGCAGAAT  ATTTCAGAAA  2280
TGTAGACTAT  CTTCTCATCC  ACGGAACAGC  AGATGATAAT  GTGCACTTTC  AAAACTCAGC  2340
ACAGATTGCT  AAAGCTCTGG  TTAATGCACA  AGTGGATTTC  CAGGCAATGT  GGTACTCTGA  2400
CCAGAACCAC  GGCTTATCCG  GCCTGTCCAC  GAACCACTTA  TACACCCACA  TGACCCACTT  2460
CCTAAAGCAG  TGTTTCTCTT  TGTCAGACTA  AAAACGATGC  AGATGCAAGC  CTGTATCAGA  2520
ATCTGAAAAC  CTTATATAAA  CCCCTCAGAC  AGTTTGCTTA  TTTTATTTTT  TATGTTGTAA  2580
AATGCTAGTA  TAAACAAACA  AATTAATGTT  GTTCTAAAGG  CTGTTAAAAA  AAAGATGAGG  2640
ACTCAGAAGT  TCAAGCTAAA  TATTGTTTAC  ATTTTCTGGT  ACTCTGTGAA  AGAAGAGAAA  2700
AGGGAGTCAT  GCATTTTGCT  TTGGACACAG  TGTTTTATCA  CCTGTTCATT  TGAAGAAAAA  2760
TAATAAAGTC  AGAAGTTCAA  AAAAAAAAA   AAAAAAAAA   AAAGCGGCCG  CTCGA       2815
```

( 2 ) INFORMATION FOR SEQ ID NO: 2:

( i ) SEQUENCE CHARACTERISTICS:
        ( A ) LENGTH: 760 amino acids
        ( B ) TYPE: amino acid
        ( D ) TOPOLOGY: linear     ( x i ) SEQUENCE DESCRIPTION: SEQ ID NO: 2:

```
Met Lys Thr Trp Val Lys Ile Val Phe Gly Val Ala Thr Ser Ala Val
                  5                  10                  15

Leu Ala Leu Leu Val Met Cys Ile Val Leu Arg Pro Ser Arg Val His
             20                  25                  30

Asn Ser Glu Glu Asn Thr Met Arg Ala Leu Thr Leu Lys Asp Ile Leu
         35                  40                  45

Asn Gly Thr Phe Ser Tyr Lys Thr Phe Phe Pro Asn Trp Ile Ser Gly
     50                  55                  60

Gln Glu Tyr Leu His Gln Ser Ala Asp Asn Ile Val Leu Tyr Asn
65                  70                  75                  80

Ile Glu Thr Gly Gln Ser Tyr Thr Ile Leu Ser Asn Arg Thr Met Lys
                 85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
    130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175

Gly Asp Pro Pro Phe Gln Ile Thr Phe Asn Gly Arg Glu Asn Lys Ile
            180                 185                 190

Phe Asn Gly Ile Pro Asp Trp Val Tyr Glu Glu Glu Met Leu Pro Thr
        195                 200                 205
```

| | | | | | | | | | | | | | | |
|---|---|---|---|---|---|---|---|---|---|---|---|---|---|---|
| Lys | Tyr | Ala | Leu | Trp | Trp | Ser | Pro | Asn | Gly | Lys | Phe | Leu | Ala | Tyr | Ala |
| 210 | | | | | 215 | | | | 220 | | | | | |
| Glu | Phe | Asn | Asp | Lys | Asp | Ile | Pro | Val | Ile | Ala | Tyr | Ser | Tyr | Tyr | Gly |
| 225 | | | | 230 | | | | 235 | | | | | | 240 |
| Asp | Glu | Gln | Tyr | Pro | Arg | Thr | Ile | Asn | Ile | Pro | Tyr | Pro | Lys | Ala | Gly |
| | | | 245 | | | | 250 | | | | | 255 | | |
| Ala | Lys | Asn | Pro | Val | Val | Arg | Ile | Phe | Ile | Ile | Asp | Thr | Thr | Tyr | Pro |
| | | 260 | | | | | 265 | | | | | 270 | | |
| Ala | Tyr | Val | Gly | Pro | Gln | Glu | Val | Pro | Val | Pro | Ala | Met | Ile | Ala | Ser |
| | 275 | | | | | 280 | | | | 285 | | | | |
| Ser | Asp | Tyr | Tyr | Phe | Ser | Trp | Leu | Thr | Trp | Val | Thr | Asp | Glu | Arg | Val |
| | 290 | | | | 295 | | | | | 300 | | | | |
| Cys | Leu | Gln | Trp | Leu | Lys | Arg | Val | Gln | Asn | Val | Ser | Val | Leu | Ser | Ile |
| 305 | | | | 310 | | | | 315 | | | | | | 320 |
| Cys | Asp | Phe | Arg | Glu | Asp | Trp | Gln | Thr | Trp | Asp | Cys | Pro | Lys | Thr | Gln |
| | | | 325 | | | | 330 | | | | | 335 | | |
| Glu | His | Ile | Glu | Glu | Ser | Arg | Thr | Gly | Trp | Ala | Gly | Gly | Phe | Phe | Val |
| | | 340 | | | | 345 | | | | | 350 | | | |
| Ser | Arg | Pro | Val | Phe | Ser | Tyr | Asp | Ala | Ile | Ser | Tyr | Tyr | Lys | Ile | Phe |
| | 355 | | | | | 360 | | | | | 365 | | | |
| Ser | Asp | Lys | Asp | Gly | Tyr | Lys | His | Ile | His | Tyr | Ile | Lys | Asp | Thr | Val |
| | 370 | | | | 375 | | | | 380 | | | | | |
| Glu | Asn | Ala | Ile | Gln | Ile | Thr | Ser | Gly | Lys | Trp | Glu | Ala | Ile | Asn | Ile |
| 385 | | | | 390 | | | | 395 | | | | | | 400 |
| Phe | Arg | Val | Thr | Gln | Asp | Ser | Leu | Phe | Tyr | Ser | Ser | Asn | Glu | Phe | Glu |
| | | | 405 | | | | 410 | | | | | 415 | | |
| Glu | Tyr | Pro | Gly | Arg | Arg | Asn | Ile | Tyr | Arg | Ile | Ser | Ile | Gly | Ser | Tyr |
| | | 420 | | | | 425 | | | | 430 | | | | |
| Pro | Pro | Ser | Lys | Lys | Cys | Val | Thr | Cys | His | Leu | Arg | Lys | Glu | Arg | Cys |
| | | 435 | | | | 440 | | | | 445 | | | | |
| Gln | Tyr | Tyr | Thr | Ala | Ser | Phe | Ser | Asp | Tyr | Ala | Lys | Tyr | Tyr | Ala | Leu |
| | 450 | | | | 455 | | | | 460 | | | | | |
| Val | Cys | Tyr | Gly | Pro | Gly | Ile | Pro | Ile | Ser | Thr | Leu | His | Asp | Gly | Arg |
| 465 | | | | 470 | | | | 475 | | | | | | 480 |
| Thr | Asp | Gln | Glu | Ile | Lys | Ile | Leu | Glu | Glu | Asn | Lys | Glu | Leu | Glu | Asn |
| | | | 485 | | | | 490 | | | | | 495 | | |
| Ala | Leu | Lys | Asn | Ile | Gln | Leu | Pro | Lys | Glu | Glu | Ile | Lys | Lys | Leu | Glu |
| | | | 500 | | | | 505 | | | | | 510 | | |
| Val | Asp | Glu | Ile | Thr | Leu | Trp | Tyr | Lys | Met | Ile | Leu | Pro | Pro | Gln | Phe |
| | | 515 | | | | | 520 | | | | | 525 | | |
| Asp | Arg | Ser | Lys | Lys | Tyr | Pro | Leu | Leu | Ile | Gln | Val | Tyr | Gly | Gly | Pro |
| | 530 | | | | | 535 | | | | | 540 | | | |
| Cys | Ser | Gln | Ser | Val | Arg | Ser | Val | Phe | Ala | Val | Asn | Trp | Ile | Ser | Tyr |
| 545 | | | | 550 | | | | 555 | | | | | | 560 |
| Leu | Ala | Ser | Lys | Glu | Gly | Met | Val | Ile | Ala | Leu | Val | Asp | Gly | Arg | Gly |
| | | | 565 | | | | | 570 | | | | | 575 | |
| Thr | Ala | Phe | Gln | Gly | Asp | Lys | Leu | Leu | Tyr | Ala | Val | Tyr | Arg | Lys | Leu |
| | | 580 | | | | | 585 | | | | | 590 | | |
| Gly | Val | Tyr | Glu | Val | Glu | Asp | Gln | Ile | Thr | Ala | Val | Arg | Lys | Phe | Ile |
| | | 595 | | | | 600 | | | | | 605 | | | |
| Glu | Met | Gly | Phe | Ile | Asp | Glu | Lys | Arg | Ile | Ala | Ile | Trp | Gly | Trp | Ser |
| | 610 | | | | | 615 | | | | | 620 | | | |
| Tyr | Gly | Gly | Tyr | Val | Ser | Ser | Leu | Ala | Leu | Ala | Ser | Gly | Thr | Gly | Leu |

|  |  |  |  | 625 |  |  |  |  | 630 |  |  |  |  | 635 |  |  |  | 640 |
| --- | --- | --- | --- | --- | --- | --- | --- | --- | --- | --- | --- | --- | --- | --- | --- | --- | --- | --- |

Phe Lys Cys Gly Ile Ala Val Ala Pro Val Ser Ser Trp Glu Tyr Tyr
              645                   650                   655

Ala Ser Val Tyr Thr Glu Arg Phe Met Gly Leu Pro Thr Lys Asp Asp
              660                   665                   670

Asn Leu Glu His Tyr Lys Asn Ser Thr Val Met Ala Arg Ala Glu Tyr
        675                   680                 685

Phe Arg Asn Val Asp Tyr Leu Leu Ile His Gly Thr Ala Asp Asp Asn
    690                   695                   700

Val His Phe Gln Asn Ser Ala Gln Ile Ala Lys Ala Leu Val Asn Ala
705                   710               715              720

Gln Val Asp Phe Gln Ala Met Trp Tyr Ser Asp Gln Asn His Gly Leu
            725               730                735

Ser Gly Leu Ser Thr Asn His Leu Tyr Thr His Met Thr His Phe Leu
        740                745              750

Lys Gln Cys Phe Ser Leu Ser Asp
      755                760

( 2 ) INFORMATION FOR SEQ ID NO: 3:

( i ) SEQUENCE CHARACTERISTICS:
        ( A ) LENGTH: 766 amino acids
        ( B ) TYPE: amino acid
        ( D ) TOPOLOGY: linear     ( x i ) SEQUENCE DESCRIPTION: SEQ ID NO: 3:

Met Lys Thr Pro Trp Lys Val Leu Leu Gly Leu Leu Gly Ala Ala Ala
              5                     10                   15

Leu Val Thr Ile Ile Thr Val Pro Val Val Leu Leu Asn Lys Gly Thr
              20                   25                   30

Asp Asp Ala Thr Ala Asp Ser Arg Lys Thr Tyr Thr Leu Thr Asp Tyr
        35                   40                 45

Leu Lys Asn Thr Tyr Arg Leu Lys Leu Tyr Ser Leu Arg Trp Ile Ser
50                  55               60

Asp His Glu Tyr Leu Tyr Lys Gln Glu Asn Asn Ile Leu Val Phe Asn
65                  70               75              80

Ala Glu Tyr Gly Asn Ser Ser Val Phe Leu Glu Asn Ser Thr Phe Asp
              85                   90                   95

Glu Phe Gly His Ser Ile Asn Asp Tyr Ser Ile Ser Pro Asp Gly Gln
            100               105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150               155              165

Gly His Lys Leu Ala Tyr Val Trp Asn Asn Asp Ile Tyr Val Lys Ile
              170               175              180

Glu Pro Asn Leu Pro Ser Tyr Arg Ile Thr Trp Thr Gly Lys Glu Asp
        185                 190              195

Ile Ile Tyr Asn Gly Ile Thr Asp Trp Val Tyr Glu Glu Glu Val Phe
            200               205                 210

Ser Ala Tyr Ser Ala Leu Trp Trp Ser Pro Asn Gly Thr Phe Leu Ala
    215                 220                 225

Tyr Ala Gln Phe Asn Asp Thr Glu Val Pro Leu Ile Glu Tyr Ser Phe
230                  235               240              245

```
Tyr  Ser  Asp  Glu  Ser  Leu  Gln  Tyr  Pro  Lys  Thr  Val  Arg  Val  Pro  Tyr
               250                      255                     260

Pro  Lys  Ala  Gly  Ala  Val  Asn  Pro  Thr  Val  Lys  Phe  Phe  Val  Val  Asn
          265                      270                     275

Thr  Asp  Ser  Leu  Ser  Ser  Val  Thr  Asn  Ala  Thr  Ser  Ile  Gln  Ile  Thr
          280                      285                     290

Ala  Pro  Ala  Ser  Met  Leu  Ile  Gly  Asp  His  Tyr  Leu  Cys  Asp  Val  Thr
     295                      300                     305

Trp  Ala  Thr  Gln  Glu  Arg  Ile  Ser  Leu  Gln  Trp  Leu  Arg  Arg  Ile  Gln
310                      315                     320                          325

Asn  Tyr  Ser  Val  Met  Asp  Ile  Cys  Asp  Tyr  Asp  Glu  Ser  Ser  Gly  Arg
               330                      335                     340

Trp  Asn  Cys  Leu  Val  Ala  Arg  Gln  His  Ile  Glu  Met  Ser  Thr  Thr  Gly
          345                      350                     355

Trp  Val  Gly  Arg  Phe  Arg  Pro  Ser  Glu  Pro  His  Phe  Thr  Leu  Asp  Gly
          360                      365                     370

Asn  Ser  Phe  Tyr  Lys  Ile  Ile  Ser  Asn  Glu  Glu  Gly  Tyr  Arg  His  Ile
     375                      380                     385

Cys  Tyr  Phe  Gln  Ile  Asp  Lys  Lys  Asp  Cys  Thr  Phe  Ile  Thr  Lys  Gly
390                      395                     400                          405

Thr  Trp  Glu  Val  Ile  Gly  Ile  Glu  Ala  Leu  Thr  Ser  Asp  Tyr  Leu  Tyr
                    410                     415                     420

Tyr  Ile  Ser  Asn  Glu  Tyr  Lys  Gly  Met  Pro  Gly  Gly  Arg  Asn  Leu  Tyr
               425                      430                     435

Lys  Ile  Gln  Leu  Ser  Asp  Tyr  Thr  Lys  Val  Thr  Cys  Leu  Ser  Cys  Glu
          440                      445                     450

Leu  Asn  Pro  Glu  Arg  Cys  Gln  Tyr  Ser  Val  Ser  Phe  Ser  Lys  Glu
          455                      460                     460

Ala  Lys  Tyr  Tyr  Gln  Leu  Arg  Cys  Ser  Gly  Pro  Gly  Leu  Pro  Leu  Tyr
465                      470                     475                          480

Thr  Leu  His  Ser  Ser  Val  Asn  Asp  Lys  Gly  Leu  Arg  Val  Leu  Glu  Asp
               485                      490                     495

Asn  Ser  Ala  Leu  Asp  Lys  Met  Leu  Gln  Asn  Val  Gln  Met  Pro  Ser  Lys
               500                      505                     510

Lys  Leu  Asp  Phe  Ile  Ile  Leu  Asn  Glu  Thr  Lys  Phe  Trp  Tyr  Gln  Met
          515                      520                     525

Ile  Leu  Pro  Pro  His  Phe  Asp  Lys  Ser  Lys  Lys  Tyr  Pro  Leu  Leu  Leu
     530                      535                     540

Asp  Val  Tyr  Ala  Gly  Pro  Cys  Ser  Gln  Lys  Ala  Asp  Thr  Val  Phe  Arg
545                      550                     555                          560

Leu  Asn  Trp  Ala  Thr  Tyr  Leu  Ala  Ser  Thr  Glu  Asn  Ile  Ile  Val  Ala
               565                      570                     575

Ser  Phe  Asp  Gly  Arg  Gly  Ser  Gly  Tyr  Gln  Gly  Asp  Lys  Ile  Met  His
               580                      585                     590

Ala  Ile  Asn  Arg  Arg  Leu  Gly  Thr  Phe  Glu  Val  Glu  Asp  Gln  Ile  Glu
          595                      600                     605

Ala  Ala  Arg  Gln  Phe  Ser  Lys  Met  Gly  Phe  Val  Asp  Asn  Lys  Arg  Ile
     610                      615                     620

Ala  Ile  Trp  Gly  Trp  Ser  Tyr  Gly  Gly  Tyr  Val  Thr  Ser  Met  Val  Leu
625                      630                     635                          640

Gly  Ser  Gly  Ser  Gly  Val  Phe  Lys  Cys  Gly  Ile  Ala  Val  Ala  Pro  Val
               645                      650                     655

Ser  Arg  Trp  Glu  Tyr  Tyr  Asp  Ser  Val  Tyr  Thr  Glu  Arg  Tyr  Met  Gly
```

660                        665                          670

Leu  Pro  Thr  Pro  Glu  Asp  Asn  Leu  Asp  His  Tyr  Arg  Asn  Ser  Thr  Val
          675                        680                      685

Met  Ser  Arg  Ala  Glu  Asn  Phe  Lys  Gln  Val  Glu  Tyr  Leu  Leu  Ile  His
     690                        695                      700

Gly  Thr  Ala  Asp  Asp  Asn  Val  His  Phe  Gln  Gln  Ser  Ala  Gln  Ile  Ser
705                      710                      715                          720

Lys  Ala  Leu  Val  Asp  Val  Gly  Val  Asp  Phe  Gln  Ala  Met  Trp  Tyr  Thr
               725                      730                           735

Asp  Glu  Asp  His  Gly  Ile  Ala  Ser  Ser  Thr  Ala  His  Gln  His  Ile  Tyr
               740                      745                      750

Thr  His  Met  Ser  His  Phe  Ile  Lys  Gln  Cys  Phe  Ser  Leu  Pro
          755                      760                      765

( 2 ) INFORMATION FOR SEQ ID NO: 4:

( i ) SEQUENCE CHARACTERISTICS:
            ( A ) LENGTH: 7 amino acids
            ( B ) TYPE: amino acid
            ( D ) TOPOLOGY: linear ( i x ) FEATURE:
            ( D ) OTHER INFORMATION: The first Xaa is either Trp or Phe.
                When the first Xaa is Trp, the second and third Xaa may
                be Glu Ile or Gly Gly. When the first Xaa is Phe, the
                second and third Xaa must be Gly Gly ( x i ) SEQUENCE DESCRIPTION: SEQ ID NO: 4:

Xaa  Gly  Trp  Ser  Tyr  Xaa  Xaa
                                    5

( 2 ) INFORMATION FOR SEQ ID NO: 5:

( i ) SEQUENCE CHARACTERISTICS:
            ( A ) LENGTH: 7 amino acids
            ( B ) TYPE: amino acid
            ( D ) TOPOLOGY: linear ( x i ) SEQUENCE DESCRIPTION: SEQ ID NO: 5:

Phe  Gly  Lys  Asp  Tyr  Gly  Gly
                                    5

( 2 ) INFORMATION FOR SEQ ID NO: 6:

( i ) SEQUENCE CHARACTERISTICS:
            ( A ) LENGTH: 7 amino acids
            ( B ) TYPE: amino acid
            ( D ) TOPOLOGY: linear ( i x ) FEATURE:
            ( D ) OTHER INFORMATION: Xaa is either Ala or Gly ( x i ) SEQUENCE DESCRIPTION: SEQ ID NO: 6:

Gly  Thr  Xaa  Asp  Asp  Asn  Val
                                    5

( 2 ) INFORMATION FOR SEQ ID NO: 7:

( i ) SEQUENCE CHARACTERISTICS:
            ( A ) LENGTH: 7 amino acids
            ( B ) TYPE: amino acid
            ( D ) TOPOLOGY: linear ( x i ) SEQUENCE DESCRIPTION: SEQ ID NO: 7:

Ala  Gln  Asn  His  Gly  Leu  Ser
                                    5

( 2 ) INFORMATION FOR SEQ ID NO: 8:

( i ) SEQUENCE CHARACTERISTICS:
( A ) LENGTH: 7 amino acids
( B ) TYPE: amino acid
( D ) TOPOLOGY: linear ( i x ) FEATURE:
( D ) OTHER INFORMATION:
The first Xaa is Glu or Ser. When the first Xaa is Glu,
the second Xaa is Gly and the third is Ala. When the
first Xaa is Ser, the second Xaa is Ser, and the third
Xaa is Arg.

( x i ) SEQUENCE DESCRIPTION: SEQ ID NO: 8:

Asp  Xaa  Asp  His  Xaa  Ile  Xaa
                      5

( 2 ) INFORMATION FOR SEQ ID NO: 9:

( i ) SEQUENCE CHARACTERISTICS:
( A ) LENGTH: 7 amino acids
( B ) TYPE: amino acid
( D ) TOPOLOGY: linear ( i x ) FEATURE:
( D ) OTHER INFORMATION:
Xaa is Pro or Ala.

( x i ) SEQUENCE DESCRIPTION: SEQ ID NO: 9:

Xaa  Thr  Ala  Asp  Glu  Lys  Ile
                      5

( 2 ) INFORMATION FOR SEQ ID NO: 10:

( i ) SEQUENCE CHARACTERISTICS:
( A ) LENGTH: 7 amino acids
( B ) TYPE: amino acid
( D ) TOPOLOGY: linear ( i x ) FEATURE:
( D ) OTHER INFORMATION:
Xaa is Thr, His or Ser.

( x i ) SEQUENCE DESCRIPTION: SEQ ID NO: 10:

Asp  Glu  Ser  His  Tyr  Phe  Xaa
                      5

We claim:

1. Isolated nucleic acid molecule which codes for mammalian FAPα having the amino acid sequence of SEQ ID NO: 2.

2. The isolated nucleic acid molecule of claim 1, consisting of nucleotides 209–2488 of the nucleotide sequence of SEQ ID NO: 1.

3. Expression vector comprising the isolated nucleic acid molecule of claim 1, operably linked to a promoter.

4. Cell line transformed or transfected by the isolated nucleic acid molecule of claim 1.

5. Cell line transformed or transfected by the expression vector of claim 3.

6. Method for determining presence of mRNA for FAPα in a cell, comprising contacting said cell with the isolated nucleic acid molecule of claim 2 under conditions favoring hybridization of said isolated nucleic acid molecule to any mRNA for FAPα present in said cell and detecting said hybridization as a determination of presence of mRNA for FAPα in said cell.

7. Process for producing mammalian FAPα comprising transfecting or transforming a host cell with an isolated nucleic acid molecule comprising a nucleotide sequence which codes for mammalian FAPα having the amino acid sequence of SEQ ID NO: 2, and culturing said host cell following transfection or transformation to produce mammalian FAPα.

8. The process of claim 7, wherein said isolated nucleic acid molecule which encodes mammalian FAPα consists of the nucleotide sequence of SEQ ID NO 1.

9. The process of claim 7, wherein said isolated nucleic acid molecule is an expression vector which comprises said nucleotide sequence which encodes FAPα, operably linked to a promoter.

10. The process of claim 7, wherein said expression vector further comprises a gene which confers antibiotic resistance on said host cell.

11. The process of claim 7, wherein said expression vector further comprises an amplifiable gene.

12. The process of claim 7, wherein said host cell is a prokaryotic cell.

13. The process of claim 12, wherein said prokaryotic cell is *E. coli*.

14. The process of claim 7, wherein said host cell is a eukaryotic cell.

15. The process of claim 14, wherein said eukaryotic cell is a yeast cell, a COS cell, or a CHO cell.

* * * * *